United States Patent [19]

Baber

[11] Patent Number: 5,139,487

[45] Date of Patent: Aug. 18, 1992

[54] LAPAROSCOPIC SURGICAL INSTRUMENT APPARATUS

[76] Inventor: Bloomfield W. Baber, 13 Elmwood Dr., Destrehan, La. 70047

[21] Appl. No.: 619,232

[22] Filed: Nov. 28, 1990

[51] Int. Cl.$^5$ ........................................... A61M 5/178
[52] U.S. Cl. .................................... 604/165; 604/164
[58] Field of Search ............... 604/264, 280, 164, 166, 604/171, 263, 158, 165; 606/108, 111, 159, 170, 209, 185

[56] References Cited

U.S. PATENT DOCUMENTS

| | | | |
|---|---|---|---|
| 3,927,660 | 12/1975 | Tegtmeyer | 604/178 X |
| 4,222,380 | 9/1980 | Terayama | 604/164 X |
| 4,326,519 | 4/1982 | D'Alo et al. | 604/177 X |
| 4,368,734 | 1/1983 | Banko | 606/170 |
| 4,393,872 | 7/1983 | Reznik et al. | 604/264 |

Primary Examiner—John J. Wilson
Assistant Examiner—Jeffrey A. Smith
Attorney, Agent, or Firm—Pravel, Gambrell, Hewitt, Kimball & Krieger

[57] ABSTRACT

An instrument which is insertable through the common tubes of a trocar, so that the distal end of the instrument may enter into the body cavity during surgery. The instrument would include an outer housing having a proximal end and a distal end, the distal end insertable through the laparoscopic instrument port, to the area of the duct to be secured a second inner housing insertable and slidably movable within the outer housing, the inner housing including a foot member extending from its distal end including an arcuate channel for enveloping and resting a portion of the duct thereupon, a member on the inner housing for securing the duct between the end of the outer housing and the arcuate channel; a third elongated member insertable through the port in the inner housing, the member including a bore throughout its length, and a point on its distal end, so that when the inner member is inserted into the bore of the inner housing, the point extends from the housing, and moves through the wall of the duct to the duct opening, so that a catheter may be inserted through the port of the interior member with the end of the catheter running into the duct through the opening made by the pointed end of the interior member.

13 Claims, 5 Drawing Sheets

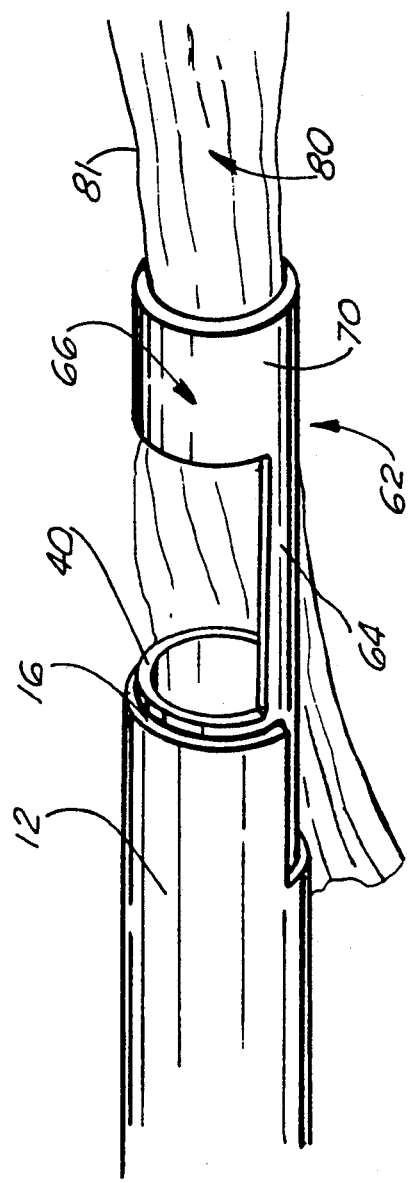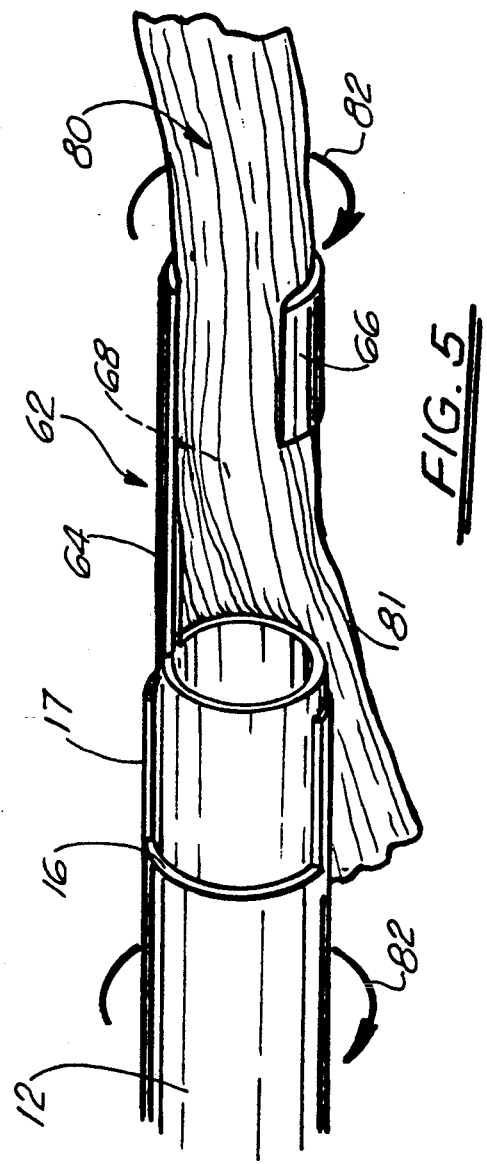

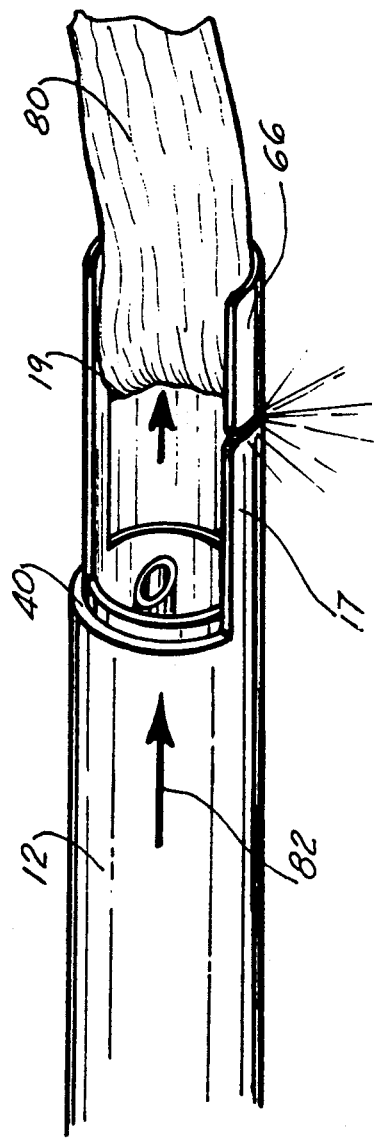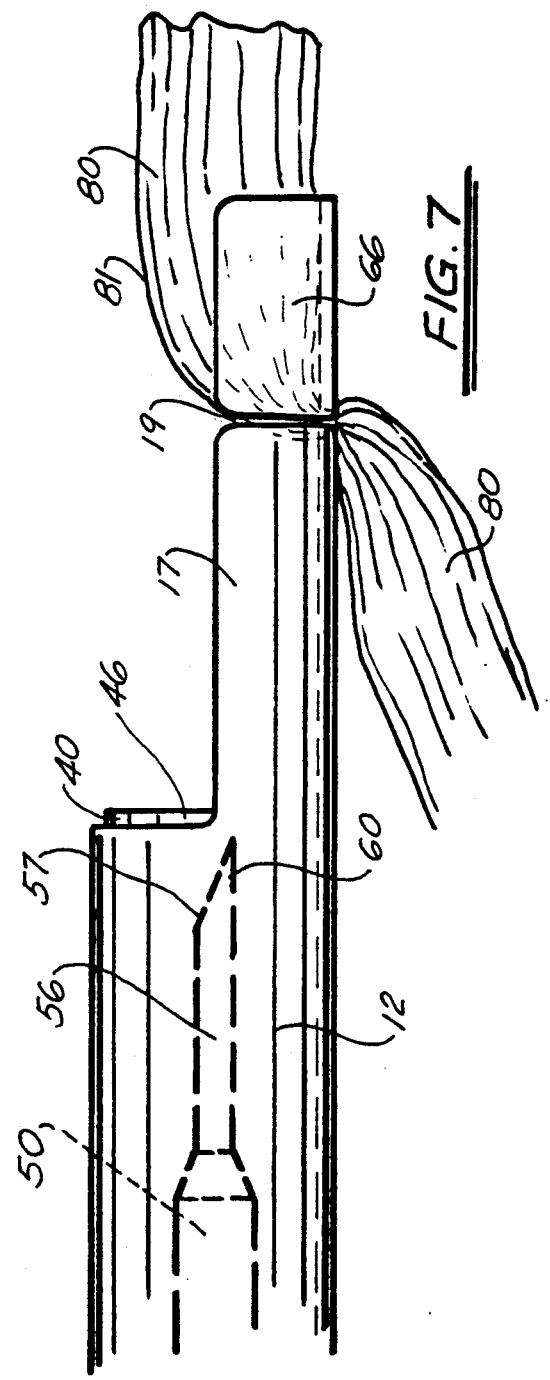

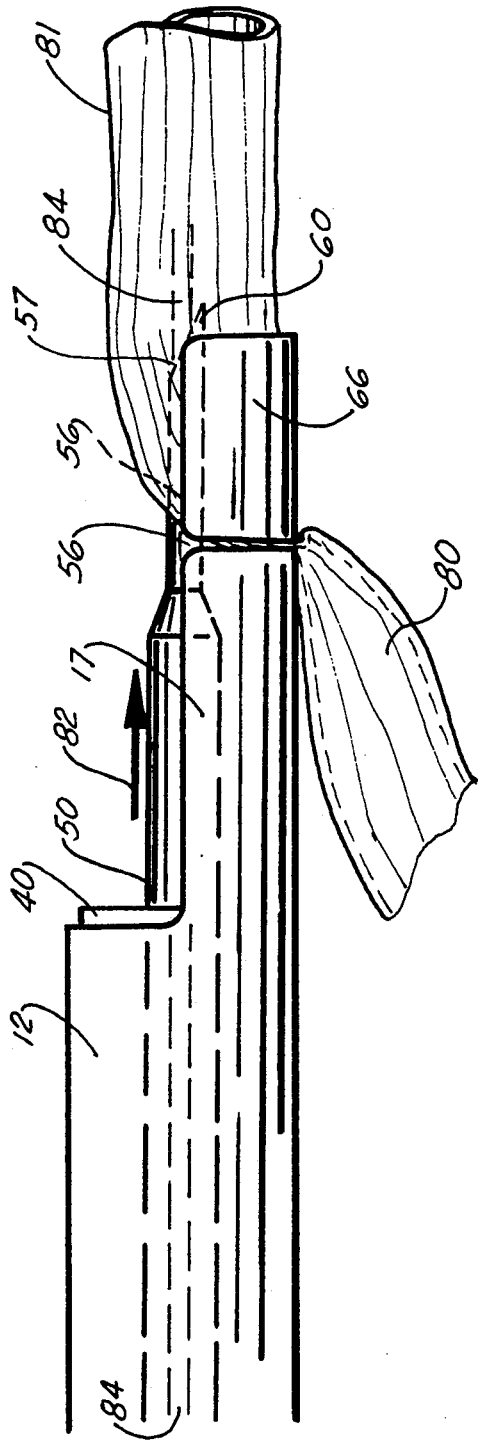
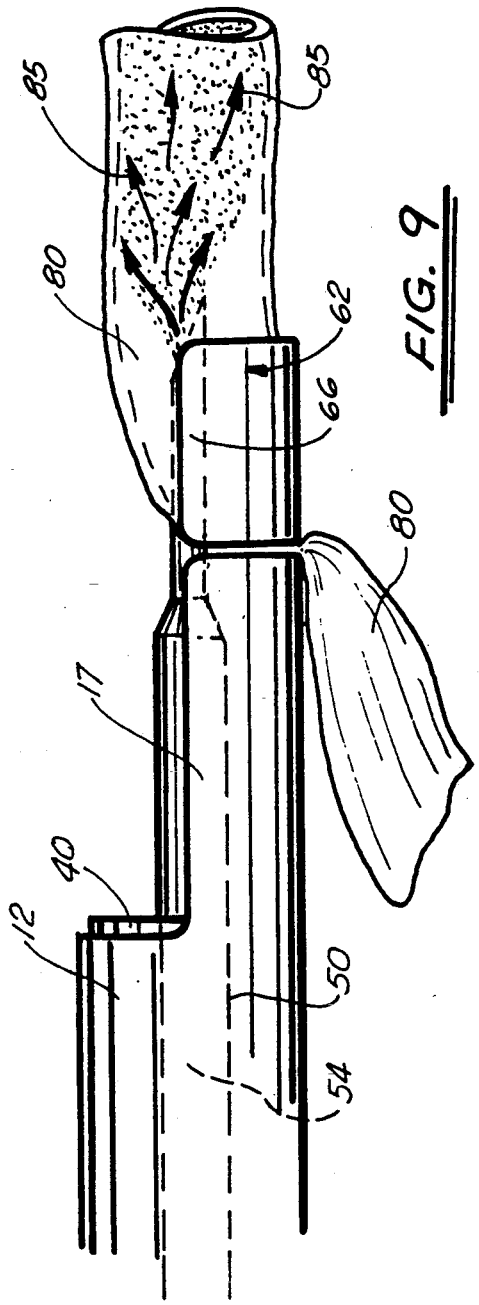

LAPAROSCOPIC SURGICAL INSTRUMENT APPARATUS

BACKGROUND OF INVENTION

1. Field Of The Invention

The present invention relates to surgical instruments. More particularly, the present invention relates to instrument utilized in laparoscopic surgery, to in the isolation of the surface of a fluid vessel so that the wall of the vessel may be pierced for the introduction of a catheter or fluids thereunto.

2. General Background

In the field of surgery, it is quite common in the present state of the art, for surgery to take place on organs or the like within the human body, without the need to work through an incision, such as the abdomen, in order to have access to the organs. What is provided, in a popular technique, is to utilize a trocar which is an instrument inserted for example, into the abdominal wall, wherein laparoscopic surgical instruments can be operated through the trocar, and the operation can be viewed by the surgeon via the use of fiberoptic techniques, on a monitor, as he maneuvers the surgical instruments through the trocar.

For example, one of the techniques wherein this process is utilized is in the removal of the gall bladder, known as cholecystectomy. In this particular operation, a trocar is inserted into the abdominal cavity, and the cavity is expanded through the introduction of gas so that there is room to maneuver in the cavity. A second trocar is inserted into the wall of the abdominal cavity so that the surgeon may utilize a pair of forceps in order to undertake the necessary techniques for the ultimate removal of the gall bladder. During the gall bladder operation, it becomes necessary for the cystic bile duct leading between the common duct and the gall bladder to be clamped off at the base of the gall bladder, so that the gall bladder may ultimately be removed. However, following the clamping off of the cystic duct, a radiocontrast must be run into the common duct to the liver to assure that there are no gallstones or the like which may block the flow of that duct. This is accomplished by making a small incision in the wall of the cystic duct, and inserting a catheter into the duct; then, injecting a radiocontrast into the duct for viewing by x-ray.

In practicing this technique called cholangiography, one must take great care in assuring that when the incision is made in the wall of the duct that the duct is not completely severed. If this happens, then the abdomen of the patient must immediately be opened, and the surgeon, through normal surgical techniques must go into the abdomen and clamp off the duct as soon as possible. Furthermore, a second problem arises if the artery which runs along side the duct, between the liver and the gall bladder, is severed when the incision is made in the duct. Therefore, it is imperative that the duct be completely isolated from the artery so no inadvertent severing of the artery will take place.

Therefore, there is need in the art for an instrument that would enable a surgeon to isolate the cystic bile duct, make a precise incision in the wall of the duct, and insert a catheter into the duct for the injection of dye into the duct passageway, in a quick and efficient manner, so that one may reduce or completely eliminate the risk of inadvertent severing of the duct or severing of the nearby artery. Several patents were found as a result of the search conducted for such an instrument. The most pertinent art found was as follows:

| PATENT NO. | INVENTOR | TITLE |
|---|---|---|
| 1,273,542 | L. Schooler | Catheter |
| 2,922,420 | P. A. Cheng | Epidural Needle |
| 3,877,434 | Ferguson et al. | Vascular Tourniquet |
| 4,049,000 | Williams | Suction Retraction Instrument |
| 4,203,429 | Vasilevsky et al. | Method of Removing Concretions From The Ureter |
| 4,372,302 | Akerlund | Instrument for Retrieval of Retracted Threads of Intrauterine Contraceptive Devices |
| 4,617,018 | Nishi | Irrigating Cannula For Extracting Lens Nucleus For Use In Extracapsular Cataract Extraction |
| 4,552,554 | Gould et al. | Introducing Catheter |
| 4,461,280 | Baumgartner | Surgical Instrument and Process |
| 4,641,652 | Hutterer et al. | Applicator for Tying Sewing Threads |
| 4,651,733 | Mobin-Uddin | Blood Vessel Holding Device And Surgical Method Using Same |
| 4,798,193 | Giesy et al. | Protective Sheath Instrument Carrier |
| 4,773,431 | Lodomirski | Intra-amniotic Loop Catheter |
| 4,769,005 | Ginsburg et al. | Selective Catheter Guide |
| 4,799,495 | Hawkins et al. | Localization Needle Assembly |
| 4,803,984 | Narayanan et al. | Method For Performing Small Vessel Anastomosis |
| 4,874,375 | Ellison | Tissue Retractor |
| 4,931,039 | Coe et al. | Ventricular Catheter Introducer |
| 4,878,487 | Sinnett | Illuminated Tissue Manipulator For Ophthalmic Surgery |

SUMMARY OF THE PRESENT INVENTION

The apparatus of the present invention solves the problem in the art in a simple and straightforward manner. What is provided is an instrument which is insertable through the common tube of a trocar, so that the instrument may enter into the body cavity during surgery. The instrument would include an outer sheath having a proximal end and a distal end, the distal end insertable through the trocar instrument port, to the area of the duct to be secured, an inner housing insertable and slidably movable within the outer sheath, the inner housing including a foot member extending from its distal end, and including an arcuate channel for enveloping and resting a portion of the duct thereupon. There is further provided means on the inner housing for securing the duct between the end of the inner housing and the foot member of the sheath; a third elongated member is insertable through a bore in the inner housing, the member including a point on its distal end, so that when the inner member is inserted into the bore of the inner housing, the point extends from the housing, and moves through the wall of the duct to the duct opening. A catheter may then be inserted through a bore through the length of the interior member with the end of the catheter running into the duct through the opening made by the pointed end of the interior member. There is also an indexing means on the proximal end of the interior member for indexing with the outer sheath, to assure that a bevel on the pointed end of the interior member is in the proper position when the pointed end is inserted into the wall of the duct. There may be further included means on the proximal end of the interior member for accommodating a syringe so that fluid may be injected directly into the bore of the interior member through the opening of the distal end of the member into the duct rather than having a catheter inserted thereunto.

Therefore, it is the principal object of the present invention to provide a surgical instrument to assist in the securing of a duct so that an incision may be made in the wall of the duct;

It is the further object of the present invention to provide a surgical instrument that is utilized in laparoscopic surgery for isolating and securing the wall of a duct, and for allowing the accurate penetration of the wall of the duct for insertion of a catheter or fluid therethrough into the lumen of the duct.

It is still a further object of the present invention to provide an instrument utilized in laparoscopic surgery which utilizes an outer sheath for the isolating of a duct, a second interior housing for securing a portion of the duct, an interior member insertable in a hollow of the inner housing, including a pointed end, for piercing the wall of that portion of the duct that is secured between the inner housing and outer sheath, for insertion of a catheter or fluid into the duct that has been secured.

It is still a further object of the present invention to provide a surgical instrument utilized in combination with laparoscopic surgery which reduces or eliminates the hazards of the piercing of the wall of a vessel or duct in the human body to prevent the inadvertent severing or other severing of the duct during the incision in the wall of the duct.

BRIEF DESCRIPTION OF THE DRAWINGS

For a further understanding of the nature and objects of the present invention, reference should be had to the following detailed description taken in conjunction with the accompanying drawings, in which like parts are given like reference numerals, and wherein:

FIGS. 4–9 illustrate detailed views of the steps undertaken in the isolating and securing, a duct and inserting a pointed instrument into the wall of the duct in the human body during laparoscopic surgery.

DETAILED DESCRIPTION OF THE PREFERRED EMBODIMENT

Figure 1:
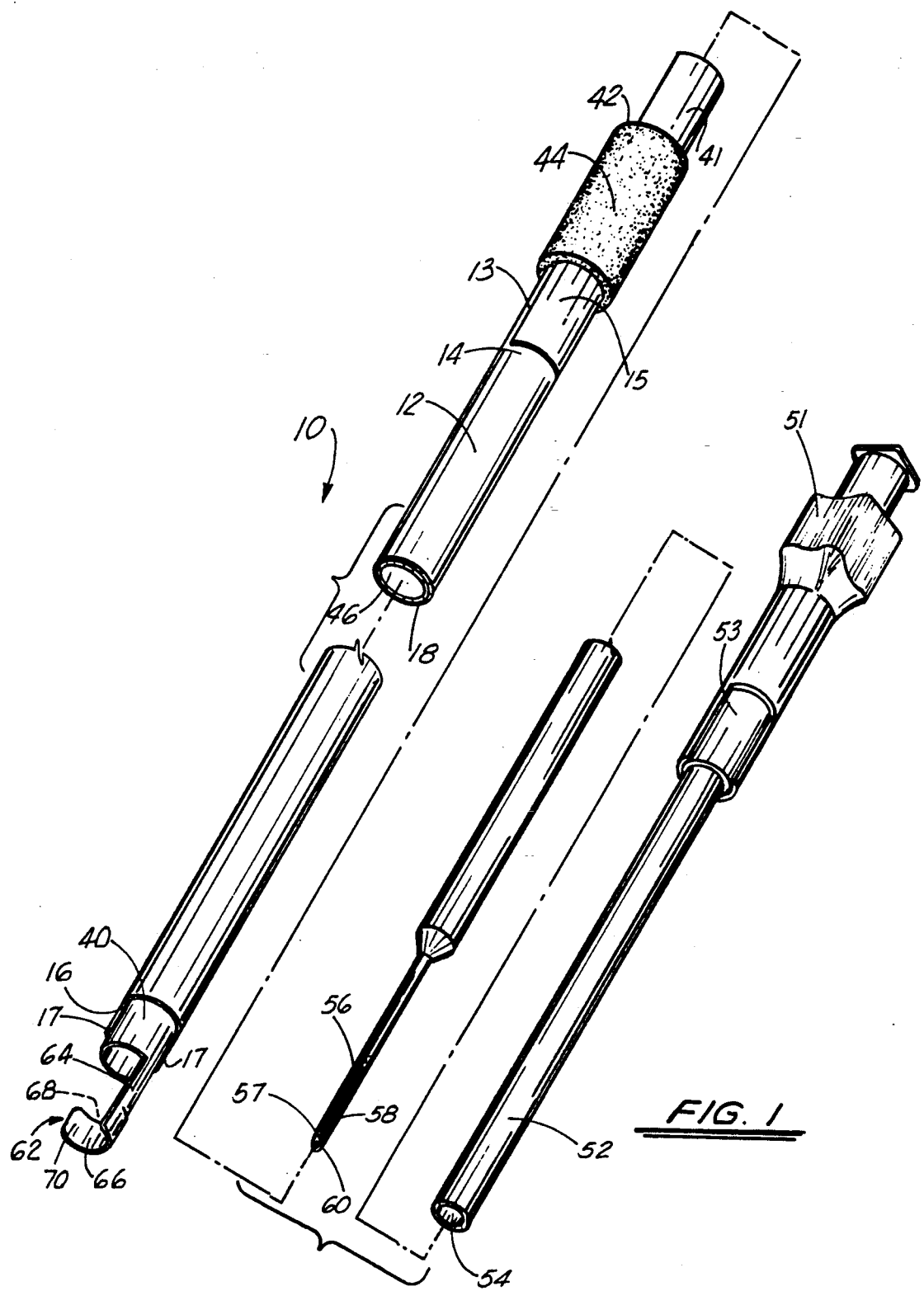
FIG. 1 illustrates an overall perspective view of the combination of the apparatus of the present invention.
Figure 2:
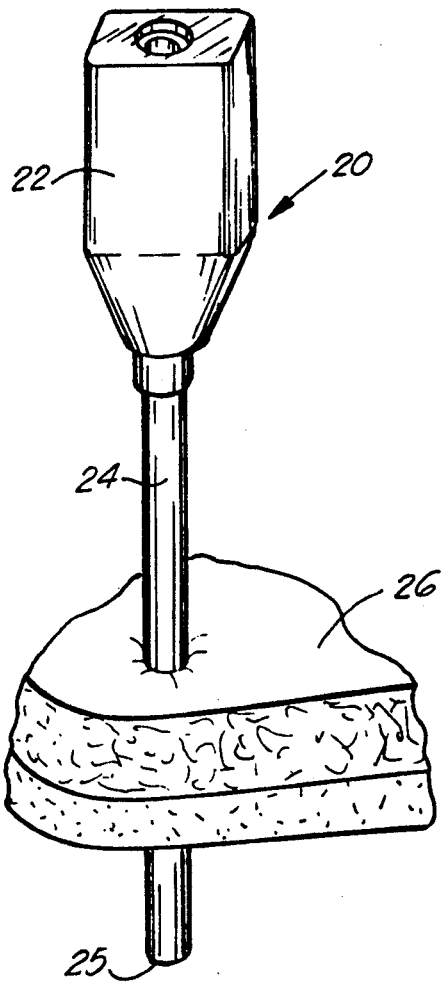
FIG. 2 illustrates a partial view of a laparoscopic trocar instrument inserted through the outer skin layer of a patient.

FIGS. 1–9 illustrate the preferred embodiment of the apparatus of the present invention, and the method for utilizing the present invention in the preferred embodiment, by the numeral 10. As illustrated, apparatus 10 comprises a first elongated outer sheath 12 having a proximal end 14 and a distal end 16 and also including a continuous bore 18 throughout the entire length of elongated sheath 12. Prior to a further discussion of the apparatus as illustrated in FIG. 1, reference is made to FIGS. 2 and 3, which illustrate a standard surgical instrument known as a trocar 20, which is common in the art, or laparoscopic surgery and includes an upper body portion 22, and a lower housing portion 24, which in utilization, the end 25 of housing 24 is inserted through the layer of skin 26 of a patient, so that surgical instruments may be utilized through the continuous bore 27 in instrument 20, and surgery can take place through the surgeon maneuvering the instruments outside of the patient, while the surgical technique takes place through the trocar instrument. This is a common surgical technique, and for purposes of this invention need not be explained further.

Figure 3:
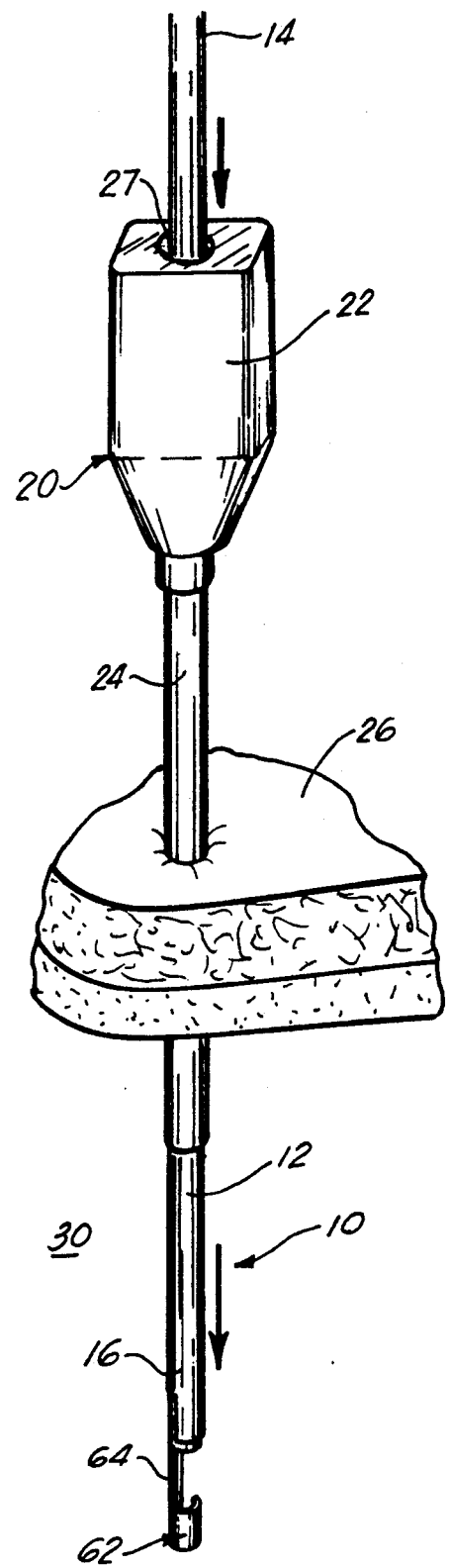
FIG. 3 illustrates an overall view of a laparoscopic trocar instrument accommodating the apparatus of the present invention.

FIG. 3, would illustrate apparatus 10 being utilized through the trocar instrument 20, in the manner in which all surgical instruments are utilized in such a technique. That is outer sheath 12 has been inserted through the housing 24 of instrument 20, with the distal end 16 of outer sheath 12 extending into, for example, the abdominal cavity 30 of the patient, so that the instrument may be utilized in the same manner as other surgical instruments in this type of surgery. Therefore, it is necessary that the length of the instrument of apparatus 10, in particular outer sheath 12, be of sufficient length so that the proximal end 14 of the sheath 12 extend out of the upper end of the housing 24 of instrument 20, while the distal end 16 of sheath 12 extend into the abdominal cavity 30 to perform its function as will be discussed further.

Returning now to the structure of the composite apparatus 10, again making reference to FIG. 1, there would be further included an inner housing 40 slidably engaged into the bore 18 of outer sheath 12, and being of sufficient length to have a proximal end portion 42 having, in the preferred embodiment, a layer of material 44 which serves as a means for grasping the proximal end of inner housing 40 during its manipulation. In addition, inner housing 40 likewise includes a bore 46 throughout its length, for accommodating a third elongated member 50, also referred to as a primary piercing member. Member 50 likewise has proximal and distal ends, a barrel portion 52, with a bore 54 therethrough for accommodating a catheter, as will be explained further. Member 50 is likewise insertable into the bore 46 of inner housing 40, during use. As illustrated, elongated member 50 would further include a pointed needle portion 56 on its distal end with needle portion 56 having a point 60 for inserting into the wall of a duct or vessel, as will be explained further.

Turning now to the relationship between outer sheath 12, inner housing 40, and elongated member 50, working in combination as apparatus 10, reference is made to the figures. As illustrated, the distal end 16 of outer sheath 12 further comprises a means for isolating and supporting a section of a vessel or duct that would be treated with the present invention. As illustrated more clearly in FIGS. 4 and 5, this means would comprise an extended foot member 62 extending outward from the distal end 16 of inner sheath 40, with the foot member 62 including an arm 64, which would culminate in a arcuate grasping portion 66, having an opening 68 in its side wall 70, the opening 68 of sufficient width in order to allow the sliding of a vessel or duct 80 resting within the grasping portion 66 as illustrated in FIG. 5.

At this point, reference should be made to the technique whereby foot member 62 would isolate and secure a duct or vessel 80 within grasping portion 66 as illustrated. In FIG. 4, there is seen duct 80, resting on the lower surface of grasping portion 66 after the duct has been slidably engaged through opening 68. Turning now to FIG. 5, upon the duct being secured as illustrated in FIG. 4, inner housing 40 is then rotated via rotation of its proximal end 42 extending outside of trocar instrument 20. Upon rotation of housing 40, and referring to FIG. 5, the opening 68 in the grasping portion 66 is then rotated so that opening 68 has been rotated to its upper most position. After that step is accomplished, reference is made to FIG. 6, wherein the outer sheath 12 is then moved forward and a lower extender portion 17 would secure duct 80 between the distal end 19 of extender 17 and the grasping portion 66 as illustrated in FIG. 7. Upon maneuvering outer sheath 10 forward in the direction of arrow 82 as illustrated in FIG. 6, duct or vessel 80 would be firmly held in place for the next step in the procedure.

As seen in FIGS. 6 and 7, while duct 80 is being secured in place between extender 17 of outer housing 12, and grasping portion 66 of inner housing 40, the interior member 50 has been inserted into the interior bore 46 of inner housing 40, as seen in the FIGURES. Following the grasping of duct 80 in place, the interior member 50 is then moved forward with the beveled edge 57 of needle portion 56 positioned upward, to assure that the beveled edge goes into the wall 81 of vessel 80 in that manner, which would facilitate a clean and clear incision into the wall as illustrated in FIG. 8. Following the insertion of the needle portion 56 into the wall 81 of vessel 80, one would then have the option of inserting a catheter 84 through the bore 54 of elongated member 50, into the vessel lumen so that dye or other liquids may be injected into the vessel.

In the alternative, and again making reference to FIG. 1, interior member 50 has on its proximal end a means 51 on the proximal end, for accommodating the barrel of a syringe, so that fluid such as medication or dye could be inserted directly into the bore 54 of elongated member 50 and being injected directly into the vessel 80 (arrows 85) as illustrated in FIG. 9, without the use of a catheter 84 as illustrated in FIG. 8.

Reference again is made to the FIGURES which also provide for an indexing means between the outer sheath 12 and the inner housing 40, when the foot member 62 has been projected forward to undertake the grasping technique that was discussed in reference to FIGS. 4 and 5. This means includes a slot 13 in the wall of outer sheath 12, wherein a protrusion 15 extending forward secured to the wall of inner housing 40 when engaged in slot 13 provides that foot member 62 be fully extended, and in the alignment necessary to begin the vessel grasping technique as was discussed. Further, there is included a second indexing means between the inner housing 40, and the interior elongated member 50, which insures that the beveled edge 57 of needle portion 56 be in the fully upright twelve o'clock position when the end 58 of needle portion 56 is inserted into the wall 81 of the duct 80. This means again includes a slot 53 in the proximal end wall of interior member 50, and a protrusion 41 extending rearedly from the proximal end of inner housing 40, so that when protrusion 41 is engaged within slot 53 of inner member 50, and foot member 62 is in the position as illustrated in FIGS. 6 and 7, the beveled surface 57 of point 60 is in the upright twelve o'clock position, ready for insertion into the wall of vessel 80.

It is through the use of this instrument as heretofore described, and the method of employing the instrument in laparoscopic surgery, which makes for a much more precise location, isolation and securing of a vessel or duct in order to make an incision in the wall of the duct for insertion of a catheter or liquid into the duct lumen.

It is foreseen that the instrument could be constructed of any material that is known safe in surgical techniques, and although it is foreseen as being used at this time in the location of a cystic bile duct in gall bladder surgery, it is foreseen that this instrument can be used on any vessel in the human body, when in fact an incision has to be made in the wall of the vessel, or some other type of opening in the vessel wall for carrying on a surgical technique. And although the apparatus of the present invention is perfectly suited for use in cholangiography, there is no intention that this instrument be limited solely for that use, but for all laparoscopic surgical techniques.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An apparatus, for use in laparoscopic surgery, to support and align a vessel to be punctured, the apparatus comprising:
    a) an outer sheath having proximal and distal end portions, and a bore therethrough;
    b) an inner housing, having proximal and distal end portions, a continuous bore therethrough, and insertable into the the bore of the outer sheath;
    c) means on the distal end of the inner housing for supporting a vessel or duct at the end of the housing when the inner housing is in axial alignment with the vessel or duct;
    d) means on the distal end of the outer sheath for securing the vessel or duct supported on the end of the inner housing between the sheath and inner housing without puncturing the vessel wall;
    e) an inner member, likewise having a bore therethrough, and slidable in the bore of the inner housing, including a pointed end portion for puncturing the wall of the supported vessel when the inner member is in axial alignment within the inner housing and with the vessel; and
    f) means insertable in the bore of the inner member for injecting a fluid through the inner member and through the puncture hole in the vessel wall.

2. The apparatus in claim 1, wherein the outer sheath is insertable into the body through a trocar surgical instrument.

3. The apparatus in claim 1, wherein the means on the inner housing for supporting the vessel or duct to be punctured further comprises a curved foot member supporting the vessel when the foot member is rotated into position around the vessel or duct wall.

4. The apparatus in claim 3, wherein there is further included indexing means between the outer sheath and inner housing to allow the foot member to support the vessel or duct wall before the vessel or duct is secured between the outer sheath and the inner housing.

5. The apparatus in claim 1, wherein there is further included a beveled wall on the pointed end portion of the inner member which must be positioned properly in order to puncture the wall of the secured vessel.

6. The apparatus in claim 5, wherein there is further included indexing means between the inner housing and the inner member to properly position the beveled wall of the inner member before the wall of the vessel is punctured.

7. The apparatus in claim 1, wherein the means on the outer sheath for securing the vessel or duct further comprises a projection which squeezes the vessel between the projection and the vessel or duct supporting means of the inner housing.

8. The apparatus in claim 1, wherein when the vessel or duct is secured, there is provided means for aligning the wall of the vessel or duct to be punctured with the movement of the point of the inner member as the inner member moves forward in the bore of the inner housing.

9. An apparatus used in laparoscopic surgery, to secure and puncture a vessel, the apparatus comprising:
   a) a primary piercing member, having a pointed end to puncture the vessel wall after the vessel has been secured;
   b) a first housing through which the primary piercing member moves from a first position within the housing to a second position puncturing the vessel wall;
   c) an outer sheath through which the first housing is positioned;
   d) means associated with the housing for securing the vessel stationary between said outer sheath and said first housing and in axial alignment with the length of the housing, so that when the primary piercing member moves to the second position, the point of the piercing member pierces the vessel wall, as the vessel is in axial alignment with the piercing member; and
   e) means for indexing the alignment between the piercing member and the housing when the piercing member moves to the second position, so that a beveled end of the piercing member is facing upward as the piercing member pierces through the vessel wall.

10. The apparatus in claim 9, wherein the means for securing the vessel stationary further comprises at least a portion of the outer sheath around the housing.

11. The apparatus in claim 9, wherein a catheter is run through a bore in the primary piercing member after the primary piercing member has punctured the vessel wall.

12. The apparatus in claim 9, wherein there is further included means for injecting a fluid directly into a bore through the primary piercing member into the vessel after the vessel wall has been punctured.

13. An instrument for securing and puncturing a vessel wall, comprising:
   a) a primary piercing member;
   b) a pointed end of the piercing member to puncture the vessel wall after the vessel has been secured;
   c) an inner housing through which the primary piercing member moves from a first position within the inner housing to a second position puncturing the vessel wall;
   d) an outer sheath within which the inner housing is positioned;
   e) means associated with the inner housing and the outer sheath for securing the vessel stationary and in axial alignment with the length of the instrument when the vessel is secured between the inner housing and the outer sheath, so that when the point of the piercing member pierces the vessel wall, the piercing member moves in alignment with the length of the vessel; and
   f) means for aligning the point of the piercing member with the vessel wall when the piercing member is moved through the bore of the inner housing and pierces the vessel wall.

* * * * *